(12) United States Patent
Caradonna et al.

(10) Patent No.: US 6,395,904 B1
(45) Date of Patent: May 28, 2002

(54) BINUCLEAR NON-HEME IRON CATALYSTS

(75) Inventors: John P. Caradonna, Wayland, MA (US); Subhasish Mukerjee, Shaker Heights, OH (US); Adonis Stassinopoulos, Concord, CA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/486,547

(22) PCT Filed: Aug. 21, 1998

(86) PCT No.: PCT/US98/17610

§ 371 (c)(1),
(2), (4) Date: Jun. 6, 2000

(87) PCT Pub. No.: WO99/10357

PCT Pub. Date: Mar. 4, 1999

Related U.S. Application Data

(60) Provisional application No. 60/056,964, filed on Aug. 26, 1997.

(51) Int. Cl.[7] .......................... C07F 15/00; C07F 13/00; C07C 35/42; C07C 233/00
(52) U.S. Cl. .......................... 548/101; 556/28; 556/45; 556/136; 556/150; 564/155; 564/158; 568/27; 568/28; 568/400; 568/401; 568/714; 568/733; 568/735; 568/744
(58) Field of Search .......................... 548/101; 556/28, 556/45, 136, 150; 564/155, 158; 568/27, 28, 400, 401, 714, 733, 735, 741

(56) References Cited

PUBLICATIONS

Stassinopoulos, et al., Binuclear Non–Heme Iron Oxo Transfer Analogue Reaction System: Observations and Biological Implications. J. Am. Chem. Soc., Sep. 12, 1990, vol. 112, No. 19, pp. 7071–7073.

(List continued on next page.)

Primary Examiner—Porfirio Nazario-Gonzalez
(74) Attorney, Agent, or Firm—Darby & Darby

(57) ABSTRACT

The subject invention provides a binuclear metal complex having structure (I) wherein $M_1$, and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl, phenyl, etc.; wherein (i) $R_1$ and $R_2$, (ii) $R_3$ and $R_4$, or (iii) $R_5$ and $R_6$ independently and optionally are linked covalently and together with the respective adjoining C atom comprise a spirocyclic ring; wherein i, j and k are integers such that $2 \leq i+j+k \leq 4$; wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene, etc., wherein said Ar is optionally substitued by $C_1$–$C_6$ alkyl or alkoxy; wherein L is N-methylimidazole, N-ethylimidazole, etc.; and wherein X is fluorine, chlorine, bromine, etc. Also provided are methods of oxidation of alkanes, arenes, and sulfides using the binuclear metal complex as a catalyst and a method of preparing said complex.

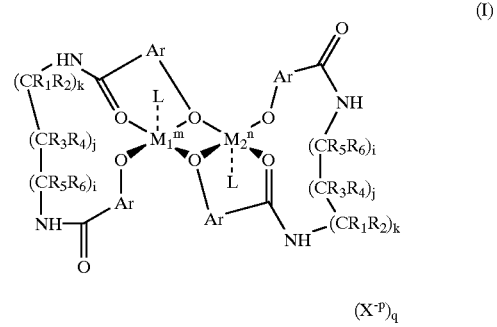

28 Claims, 1 Drawing Sheet

OTHER PUBLICATIONS

Stassinopoulos et al., Synthesis Structure and Electronic Characterization of Reactive Diiron (II) 1,2–Bis(21–hydroxybenzamido)benzene Complexes as Models for Methane Monooxygenase. J. Am. Chem. Soc., Nov. 6, 1991, vol. 113, No. 23, pp. 8686–8697.

Sunatsuki et al., Dinaionic Ligand complexes K2[CuLn] and K2[NiLn] (n=1,2; H4L1=1, 2–Bis(2–hydroxybenzamido)ethane, H4L2=1, 2–Bis(2–hydroxybenzamido)benzene), and Their Dinuclear Cu(II)–Cu(II) and Ni(II)–Cu(II) Complexes, Bull. Chem. Soc. Japan, Aug. 1997, vol. 70, No. 8, pp. 1851–1858.

Nguyen et al., [FeIII(PMA)]2+: A Mononuclear Non–Heme Iron Complex That Catalyzes Alkane Oxidation. Inorg. Chem., Oct. 9, 1996, vol. 35, No. 21 pp. 6273–6281.

BINUCLEAR NON-HEME IRON CATALYSTS

This application claims benefit of provisional application ser. No. 60/056,964 filed Aug. 26, 1997.

This invention was made with government support under grant no. SGER CHE-949178 from the National Science Foundation and grant no. R29GM49871 from the National Institutes of Health. Accordingly, the U.S. Government has certain rights in the invention.

FIELD OF THE INVENTION

The present invention is in the field of binuclear non-heme iron compounds. In particular, the invention relates to binuclear iron compounds which are useful as catalysts in the oxidation of various organic substances, such as alkanes, arenes, olefins and sulfides. The invention further relates to a method for preparing alcohols from alkanes, or arenes, epoxides from olefins, ketones from alkanes, sulfoxides and sulfones from sulfides using the binuclear iron compounds.

BACKGROUND OF THE INVENTION

As known petroleum reserves are rapidly depleted, a need exists to secure an alternative source of industrial chemical feedstocks now derived from oil. One approach is to convert relatively abundant coal and natural gases such as methane into synthesis gas, a mixture of carbon monoxide and hydrogen, which can then be transformed into alcohols, acids, esters, etc. Accordingly, the need remains to provide efficient methods to convert hydrocarbons directly into oxidized organics.

Binuclear non-heme iron centers such as those found in the active site of methane monooxygenase (MMO) act as oxygen atom transfer catalysts by a complex, poorly understood mechanism.[1,2] Despite advances in understanding the structural,[3] spectroscopic,[4,5] and mechanistic aspects of enzymatic alkane oxidation,[4,5] attempts to effect hydrocarbon oxidation by a biomimetic mechanism have not succeeded.[1,2] While synthetic non-heme diferric systems are reported to oxygenate substrates in the presence of either dioxygen[6] or alkyl peroxides,[1,2,4,5,7-13] the peroxide chemistry is now thought to be dominated by oxygen-based free radical pathways.[14-17]

The present invention provides a catalytically competent binuclear non-heme Fe complexes that can perform biologically relevant oxo-atom transfer chemistry.[18,19] Specifically, the invention provides compounds of the formula [$Fe_2^{2+}$ ($H_2Hbamb$)$_2$(N-MeIm)$_2$], 1, [$Fe^{2+}$, $Fe^{2+}$], Scheme 1),[20a] as well as its mixed-valence [$Fe^{2+}$, $Fe^{3+}$], 2, and diferric [$Fe^{3+}$, $Fe^{3+}$], 3, core states, all of which possess remarkable reactivity properties. Thus, both the [$Fe^{2+}$, $Fe^{2+}$], 1, and [$Fe^{2+}$, $Fe^{3+}$], 2, complexes are uniquely capable of catalyzing the oxidation of alkanes, alkenes and sulfides by the known oxygen atom donor, iodosylbenzene (OIPh). The catalytic chemistry of non-heme 1 and 2 parallel that reported for cytochrome P-450, a system believed to involve a porphyrin cation radical ($Fe^{4+}$=O) reactive intermediate.[21-23]

SUMMARY OF THE INVENTION

Accordingly, one object of the present invention is to provide a binuclear metal complex having the structure:

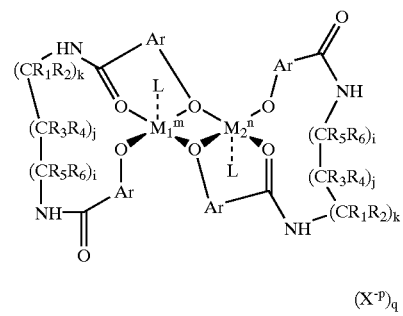

wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate.

Another object of the present invention is to provide a ligand having the structure:

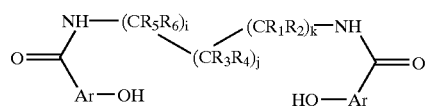

wherein $R_1$, $R_2$, $R_3$, $R_4$, $R_5$ and $R_6$ are independently and optionally substituted linear $C_1$–$C_6$ alkyl, $C_5$–$C_6$ cycloalkyl or phenyl; wherein $R_1$, $R_2$, $R_3$, $R_4$, $R_5$ and $R_6$ are independently a linear $C_1$–$C_6$ alkyl $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate.

A further object of the invention is to provide a method of preparing an alcohol from an alkane or cycloalkane wherein said alkane or cycloalkane is optionally substituted by an aryl, which comprises:

(A) dissolving the alkane or cycloalkane in a suitable solvent to form a solution; and (B) treating the solution with an oxygen atom donor in the presence of a binuclear metal complex having the structure:

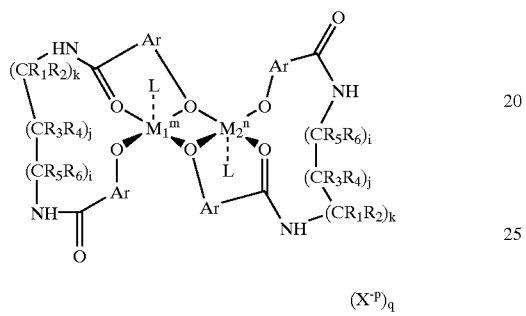

$(X^{-p})_q$ wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the alcohol.

A further object is to provide a method of preparing an epoxide from an alkene or cycloalkene, wherein the alkene or cycloalkane is optionally mono-, di-, tri- or tetrasubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

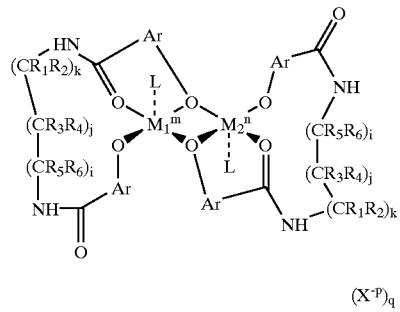

$(X^{-p})_q$ wherein $M_1$ and $M_2$ are independently selected from the group consisting of Fe, Co, Mn and Ru; wherein m+n is +4 or +5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; where in Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the epoxide.

An additional object is to provide a method of preparing a sulfoxide from a dialkyl sulfide, alkyl aryl sulfide or diaryl sulfide wherein each alkyl is independently an optionally substituted $C_1$–$C_6$ alkyl, $C_3$–$C_9$ alkylalkenyl, or $C_5$–$C_6$ cycloalkyl, or the sulfide S atom interrupts an optionally substituted $C_5$–$C_{10}$ alkane ring, which comprises:

(A) dissolving the sulfide in a suitable solvent to form a solution; and (B) treating the solution with an oxygen atom donor in the presence of a binuclear metal complex having the structure:

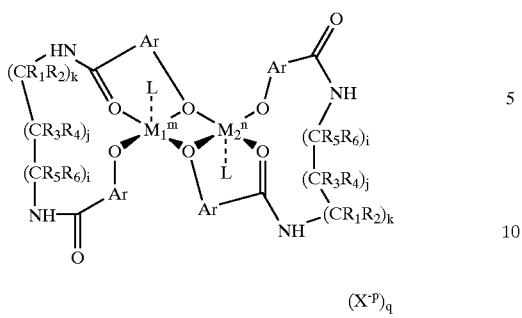

$(X^{-p})_q$ wherein $M_1$ and $M_2$ are independently selected from the group consisting of Fe, Co, Mn and Ru; wherein m+n is +4 or +5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein is 1 or 2, and q is 0, 1 or 2 such that m+n −4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the sulfoxide.

Another object of the invention is to provide a method of preparing an arene alcohol from an arene wherein said arene is optionally substituted by an aryl, which comprises:

(A) dissolving the arene in a suitable solvent to form a solution; and (B) treating the solution with an oxygen atom donor in the presence of a binuclear metal complex having the structure:

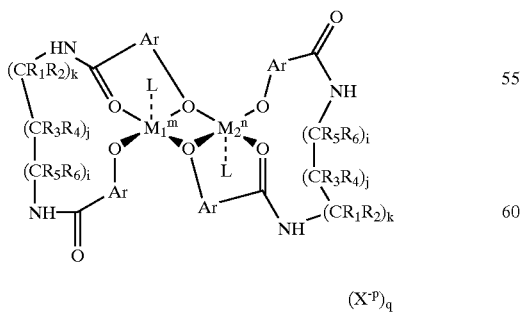

$(X^{-p})_q$ wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the arene alcohol.

Another object of the invention is to provide a method of preparing a sulfone from a dialkyl sulfide, alkyl aryl sulfide or diaryl sulfide wherein each alkyl is independently an optionally substituted $C_1$–$C_6$ alkyl, $C_3$–$C_9$ alkylalkenyl, or $C_5$–$C_6$ cycloalkyl, or the sulfide S atom interrupts an optionally substituted $C_5$–$C_{10}$ alkane ring, which comprises:

(A) dissolving the sulfide in a suitable solvent to form a solution; and (B) treating the solution with an oxygen atom donor in the presence of a binuclear metal complex having the structure:

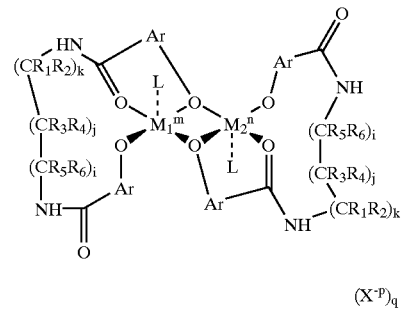

$(X^{-p})_q$ wherein $M_1$ and $M_2$ are independently selected from the group consisting of Fe, Co, Mn and Ru; wherein m+n is +4; wherein p is 1 or 2, and q is 0, 1 or 2 such that m+n−4=p×q; wherein $R_1$, $R_2$, $R_3$, $R_4$, $R_5$ and $R_6$ are independently an optionally substituted linear $C_1$–$C_6$ alkyl, $C_5$–$C_6$ cycloalkyl or phenyl; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i,j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene; wherein L is N-methylimidazole, N-ethylimidazole, N-1-propylimidazole or N-phenylimidazole, and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the sulfone.

Another object is to provide a method of preparing a alcohol from an alkene or cycloalkene wherein said alkene or cycloalkene is optionally mono-, di- or trisubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

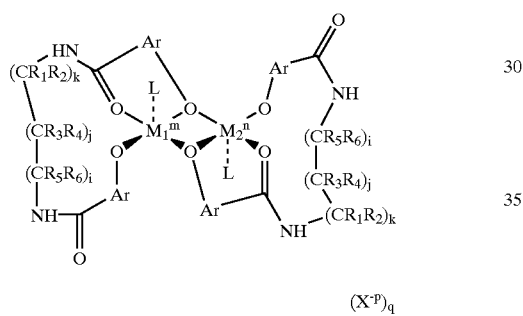

wherein $M_1$ and $M_2$ are independently selected from the group consisting of Fe, Co, Mn and Ru; wherein m+n is 4 or 5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the alcohol.

Another object is to provide a method of preparing a ketone from an alkene or cycloalkene wherein said alkene or cycloalkene is optionally mono-, di- or trisubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

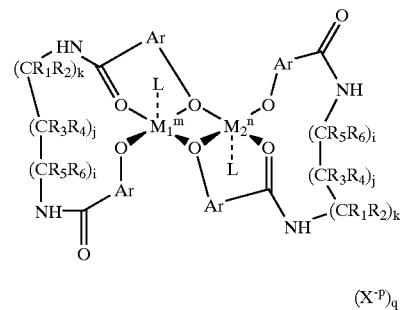

wherein $M_1$ and $M_2$ are independently selected from the group consisting of Fe, Co, Mn and Ru; wherein m+n is 4 or 5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the ketone.

A final object of the invention is to provide a method of preparing a binuclear metal complex having the structure:

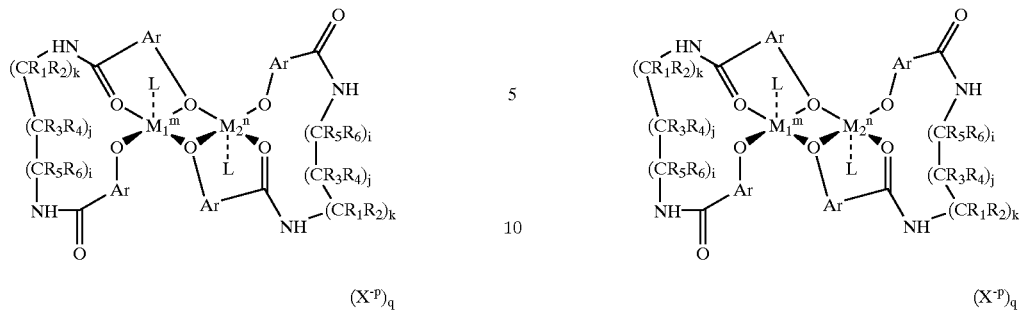

wherein $M_1$ and $M_2$ are independently selected from the group consisting of Fe, Co, Mn and Ru; wherein m and n are independently 2 or 3; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, which comprises:

(A) preparing a dilithio, disodio or dipotassio salt of a ligand having the structure:

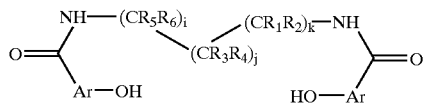

wherein $R_1$, $R_2$, $R_3$, $R_4$, $R_5$, $R_6$, i, j, k and Ar are defined as above; and (B) contacting the salt formed in step (A) with an approximately equal amount of $\{M_1^m/M_2^n\}(L)_2(X^{-P})_q(S)_2$ wherein $M_1$, $M_2$, L and X are defined as above; wherein m and n are each +2; and p×q=m or n; wherein S is a solvent selected from the group consisting of a linear or branched alkyl alcohol and water; under suitable conditions to form the binuclear metal complex.

DETAILED DESCRIPTION OF THE INVENTION

Figure 1:
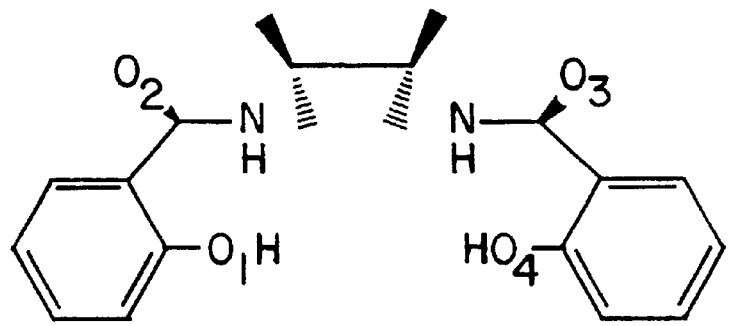
FIG. 1 is an illustration of the structure of 2,3-bis(2-hydroxybenzamido)-2,3-dimethylbutane ($H_4$Hbamb).
Figure 2:
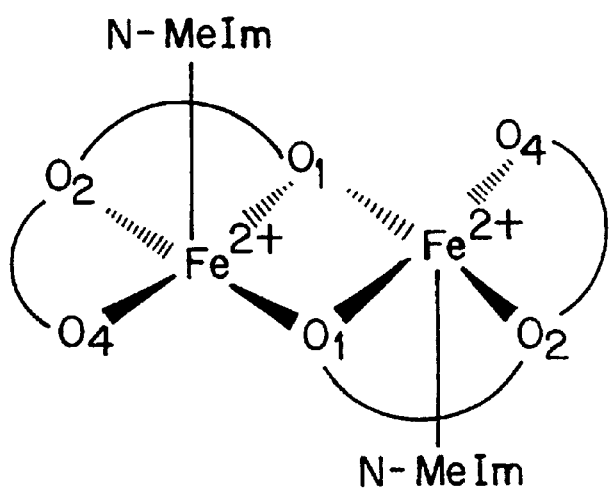
FIG. 2 is an illustration of the structure of compex 1, $[Fe_2^{2f}(H_2Hbamb)_2(N\text{-MeIm})_2]$.

The present invention provides a binuclear metal complex having the structure:

wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate.

In one embodiment, the invention provides a binuclear complex as illustrated above wherein the complex is optically active. In another embodiment, the binuclear complex is provided wherein $M_1$ and $M_2$ are Fe; wherein m and n are +2; wherein i and j are 1, and k is 0; and $R_1$, $R_2$, $R_3$, $R_4$, $R_5$ or $R_6$ are methyl. In a particular embodiment, the ligand L is N-methylimidazole.

The binuclear metal complexes of the invention either have no axial ligands in the sixth coordination site or have non-coordinating or weakly coordinating ligands. Among the weakly coordinating ligands are solvent molecules, such as tetra-hydrofuran, and anions derived from weak or strong organic or inorganic acids, such as benzoic acid, boric acid and sulfuric acid.

In the compounds of the invention, alkyl groups and the alkyl moiety of alkoxy groups can be in the form of straight or branched chains (if larger than 3 carbon atoms) and preferably contain 1 to 6 carbon atoms, more preferably 1 to 4 carbon atoms. Examples are methyl, ethyl, propyl (n- and iso-propyl) and butyl (n-, sec-, iso- and tert-butyl). Optional substituents of alkyl include hydroxy, halogen (especially chlorine or fluorine) and alkoxycarbonyl. Trifluoromethyl is an optionally substituted alkyl group of particular interest.

Cycloalkyl, which is preferably $C_3$–$C_6$ cycloalkyl, includes cyclohexyl and cycloalkylalkyl, which is preferably $C_3$–$C_6$ cycloalkyl($C_1$–$C_4$)alkyl, includes cyclopropylethyl. An example of a cycloalkyl group containing a heteroatom is tetrahydropyranyl.

Ar may be substituted by alkyl, including phenylalkyl (especially benzyl, phenylethyl, phenylpropyl, phenylbutyl or phenylhexyl) in which the alkyl moiety may carry other substituents such as hydroxy and the aryl moiety may be substituted with, for example, one or more of the following; halogen, hydroxy, $C_1$–$C_4$ alkyl (especially methyl and ethyl), $C_1$–$C_4$ alkoxy (especially methoxy), halo($C_1$–$C_4$) alkyl (especially trifluoromethyl), halo($C_1$–$C_4$)alkoxy (especially trifluoromethoxy), $C_1$–$C_4$ alkylthio (especially methylthio), $C_1$–$C_4$ alkoxy($C_1$–$C_4$)alkyl, $C_3$–$C_6$ cycloalkyl, $C_3$–$C_6$ cycloalkyl($C_1$–$C_4$)alkyl, aryl (especially phenyl), aryloxy (especially phenyloxy), aryl($C_1$–$C_4$)alkyl (especially benzyl, phenylethyl and phenyl n-propyl), aryl ($C_1$–$C_4$)alkoxy (especially benzyloxy), aryloxy($C_1$–$C_4$) alkyl (especially phenyloxymethyl), carbacyl (especially acetyloxy and benzoyloxy), cyano, thiocyanato, nitro, —NR'R", —NHCOR', —NHCONR'R", —CONR'R", —COOR", —OSO2R', —SO$_2$R', —COR', —CR'=NR" or —N=CR'R" in which R' and R" are independently hydrogen, $C_1$–$C_4$ alkyl, $C_1$–$C_4$ alkoxy, $C_1$–$C_4$ alkylthio, $C_3$–$C_6$ cycloalkyl, $C_3$–$C_6$ cycloalkyl($C_1$–$C_4$)alkyl, phenyl or benzyl, the phenyl and benzyl groups being optionally substituted with halogen, $C_1$–$C_4$ alkyl or $C_1$–$C_4$ alkoxy.

Aryl is preferably phenyl, and may encompass heteroaryl, which includes such heteroaromatic groups such as pyridinyl, pyrimidinyl, pyrazinyl, pyridazinyl, 1,2,3-, 1,2,4-, and 1,3,5-triazinyl, 1,2,4,5-tetrazinyl, thienyl, quinolinyl, isoquinolinyl, quinoxalinyl and benzothiophenyl. Aryl may be substituted by one to four groups selected from the group consisting of $C_1$–$C_6$ alkyl or alkoxy groups, acyl, acylamino, iodine, fluorine, bromine and chlorine.

Acylamino and acyl may be optionally substituted by such groups as —NR'R", —NHCOR and —COR' in which R' and R" are as defined above. Acyl includes, in particular, formyl, acetyl and benzoyl, and acylamino includes benzoylamino and furoylamino optionally substituted by, for example, N—($C_1$–$C_4$)alkyl (especially N-methyl).

The invention also provides a ligand having the structure:

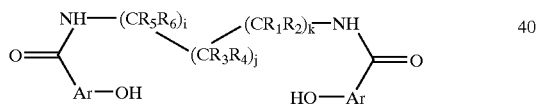

wherein $R_1$, $R_2$, $R_3$, $R_4$, $R_5$ and $R_6$ are independently and optionally substituted linear $C_1$–$C_6$ alkyl, $C_5$–$C_6$ cycloalkyl or phenyl; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate. In a certain embodiment, the ligand wherein i and j are 1, and k is 0; and $R_1$, $R_2$, $R_3$, $R_4$, $R_5$ and $R_6$ are methyl. More preferably, $R_1$, $R_2$, $R_3$, $R_4$, $R_5$ or $R_6$ are all hydrogen.

The present invention provides a method of preparing an alcohol from an alkane or cycloalkane wherein said alkane or cycloalkane is optionally substituted by an aryl, which comprises:

(A) dissolving the alkane or cycloalkane in a suitable solvent to form a solution; and (B) treating the solution with an oxygen atom donor in the presence of a binuclear metal complex having the structure:

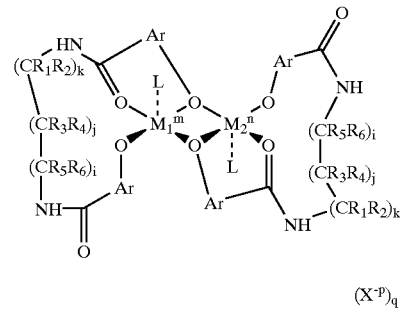

wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the alcohol.

In one embodiment, the invention provides the method as disclosed wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

In the practice of the invention, alkanes which are useful as substrates for the method of oxidation may be linear, branched or cyclic, and may be liquid or gaseous. Preferably, the alkane is methane, ethane, n-propane, iso-propane, n-butane, iso-butane or n-pentane. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

The present invention also provides a method of preparing an epoxide from an alkene or cycloalkene, wherein the alkene or cycloalkane is optionally mono-, di-, tri- or tetrasubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

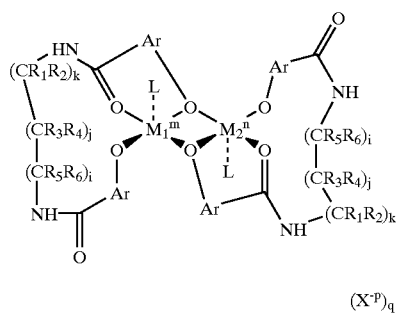

wherein $M_1$ and $M_2$ are independently selected from the group consisting of Fe, Co, Mn and Ru; wherein m+n is +4 or +5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the epoxide.

In one embodiment, the method is practiced using an oxygen atom donor selected from the group consisting of iodosyl benzene, a peracid, N,N-dimethylaniline N-oxide, N,N-dimethyl-p-cyanoaniline N-oxide, periodate, t-butyl hydroperoxide, a peroxide and hypochlorite ion. In another embodiment, the complex used in the method is optically active and the epoxide prepared is a single enantiomer.

In the practice of the invention, alkenes which are useful as substrates for the method of oxidation may be linear, branched or cyclic, and may be liquid or gaseous. Preferably, the alkene is ethene, propene, iso-propylene, 1-butene, iso-butylene or 1-pentene. Also of interest as substrates are alkenes and cycloalkenes which are synthetic intermediates along pathways to prepare organic natural products. Cycloalkenes useful as substrates include cyclopropene, cyclobutene, cyclopentene, cyclohexene, and cycloheptene. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

The present invention further provides a method of preparing a sulfoxide from a dialkyl sulfide, alkyl aryl sulfide or diaryl sulfide wherein each alkyl is independently an optionally substituted $C_1$–$C_6$ alkyl, $C_3$–$C_9$ alkylalkenyl, or $C_5$–$C_6$ cycloalkyl, or the sulfide S atom interrupts an optionally substituted $C_5$–$C_{10}$ alkane ring, which comprises:

(A) dissolving the sulfide in a suitable solvent to form a solution; and (B) treating the solution with an oxygen atom donor in the presence of a binuclear metal complex having the structure:

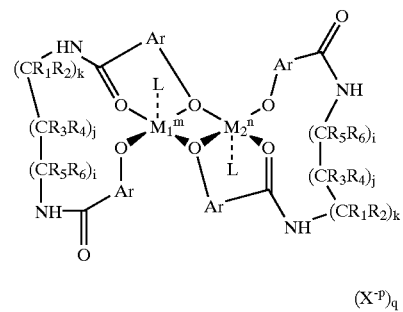

wherein $M_1$ and $M_2$ are independently selected from the group consisting of Fe, Co, Mn and Ru; wherein m+n is +4 or +5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that $m+n-4=p\times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the sulfoxide.

In a certain embodiment, the oxygen atom donor used in the method is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

In the practice of the invention, dialkyl sulfides which are useful as substrates for the method of oxidation may be linear, branched or cyclic. Preferably, the dialkyl sulfide is dimethyl sulfide, methyl ethyl sulfide, methyl cyclopentyl sulfide, methyl cyclohexyl sulfide, methyl cyclopenylmethyl sulfide, methyl cyclohexylmethyl sulfide, diethyl sulfide, n-propyl methyl sulfide, iso-propyl methyl sulfide, etc. Cyclic alkyl sulfides include thiirane, thietane, thiolane and thiane, either as isolated ring systems or fused onto hydrocarbon rings. Alkyl aryl sulfides useful as substrates include methyl phenyl sulfide, methyl 4-methylphenyl sulfide, methyl 2,4-dimethylphenyl sulfide, ethyl phenyl sulfide, n-propyl phenyl sulfide, isopropyl phenyl sulfide, methyl naphthyl sulfide, etc. Diaryl sulfides useful as substrates include diphenyl sulfide, phenyl 3-methylphenyl sulfide, phenyl 2,4-dimethylphenyl sulfide, di(4-methylphenyl) sulfide, etc. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

The present invention also provides a method of preparing an arene alcohol from an arene wherein said arene is optionally substituted by an aryl, which comprises:

(A) dissolving the arene in a suitable solvent to form a solution; and (B) treating the solution with an oxygen atom donor in the presence of a binuclear metal complex having the structure:

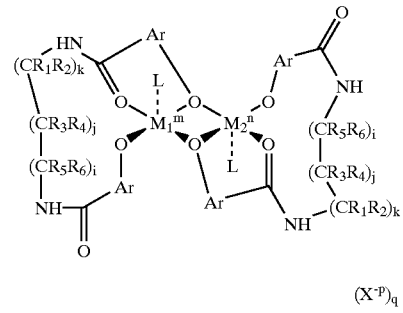

$(X^{-p})_q$ wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that $m+n-4=p\times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the arene alcohol.

In one embodiment, the method as disclosed is practiced using as the oxygen atom donor either iodosyl benzene, a peracid, N,N-dimethylaniline N-oxide, N,N-dimethyl-p-cyanoaniline N-oxide, periodate, t-butyl hydroperoxide, a peroxide or hypochlorite ion. The arene hydroxylation is typically practiced using a variety of arene substrates including benzene, napthalene, anthracene or indene.

In the practice of the invention, arenes which are useful as substrates for the method of oxidation may be monocyclic or fused multicyclics. Preferably, the arene is benzene, naphthalene, anthracene, indene, and the like. In addition, the arene may be fused onto a larger multiring system which is an intermediate in a synthetic pathway to prepare a compound of interest. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

The present invention additionally provides a method of preparing a sulfone from a dialkyl sulfide, alkyl aryl sulfide or diaryl sulfide wherein each alkyl is independently an optionally substituted $C_1$–$C_6$ alkyl, $C_3$–$C_9$ alkylalkenyl, or $C_5$–$C_6$ cycloalkyl, or the sulfide S atom interrupts an optionally substituted $C_5$–$C_{10}$ alkane ring, which comprises:
(A) dissolving the sulfide in a suitable solvent to form a solution; and
(B) treating the solution with an oxygen atom donor in the presence of a binuclear metal complex having the structure:

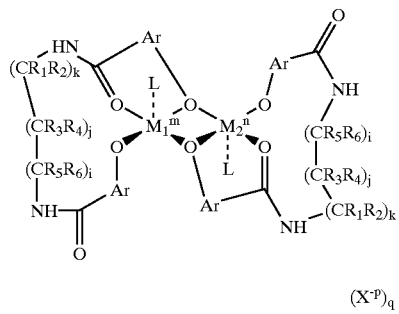

wherein $M_1$ and $M_2$ are independently selected from the group consisting of Fe, Co, Mn and Ru; wherein m+n is +4; wherein p is 1 or 2, and q is 0, 1 or 2 such that m+n−4=p×q; wherein $R_1$, $R_2$, $R_3$, $R_4$, $R_5$ and $R_6$ are independently an optionally substituted linear $C_1$–$C_6$ alkyl, $C_5$–$C_6$ cycloalkyl or phenyl; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that 2≦i+j+k≦4; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the sulfone.

In one embodiment, the oxygen atom donor used in the method is iodosyl benzene, a peracid, N,N-dimethylaniline N-oxide, N,N-dimethyl-p-cyanoaniiline N-oxide, periodate, t-butyl hydroperoxide, a peroxide or hypochlorite ion.

In the practice of the invention, dialkyl sulfides which are useful as substrates for the method of oxidation may be linear, branched or cyclic. Preferably, the dialkyl sulfide is dimethyl sulfide, methyl ethyl sulfide, methyl cyclopentyl sulfide, methyl cyclohexyl sulfide, methyl cyclopenylmethyl sulfide, methyl cyclohexylmethyl sulfide, diethyl sulfide, n-propyl methyl sulfide, iso-propyl methyl sulfide, etc. Cyclic alkyl sulfides include thiirane, thietane, thiolane and thiane, either as isolated ring systems or fused onto hydrocarbon rings. Alkyl aryl sulfides useful as substrates include methyl phenyl sulfide, methyl 4-methylphenyl sulfide, methyl 2,4-dimethylphenyl sulfide, ethyl phenyl sulfide, n-propyl phenyl sulfide, isopropyl phenyl sulfide, methyl naphthyl sulfide, etc. Diaryl sulfides useful as substrates include diphenyl sulfide, phenyl 3-methylphenyl sulfide, phenyl 2,4-dimethylphenyl sulfide, di(4-methylphenyl) sulfide, etc. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

The present invention also provides a method of preparing a alcohol from an alkene or cycloalkene wherein said alkene or cycloalkene is optionally mono-, di- or trisubstituted independently with an optionally substituted linear $C_1$–$C_6$ alkyl, $C_5$–$C_6$ cycloalkyl or phenyl, which comprises:
(A) dissolving the alkene or cycloalkene in a suitable solvent to form a solution; and
(B) treating the solution with an oxygen atom donor in the presence of a binuclear metal complex having the structure:

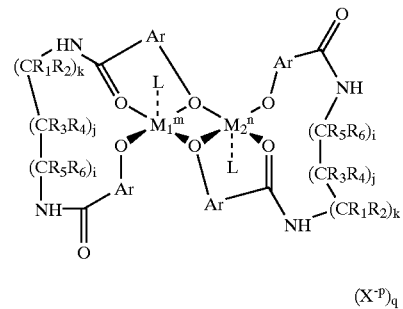

wherein $M_1$ and $M_2$ are independently selected from the group consisting of Fe, Co, Mn and Ru; wherein m+n is 4 or 5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i,j and k are integers such that $2 \leq i+j+k \leq 4$; wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the alcohol.

In one embodiment, the oxygen atom donor used in the method is iodosyl benzene, a peracid, N,N-dimethylaniline N-oxide, N,N-dimethyl-p-cyanoaniline N-oxide, periodate, t-butyl hydroperoxide, a peroxide or hypochlorite ion. In another embodiment, the method is practiced as taught above but the complex is optically active in which case the alcohol is generated as a single enantiomer.

In the practice of the invention, alkenes which are useful as substrates for the method of oxidation have a free allylic substitution site, and may be linear, branched or cyclic, and may be liquid or gaseous. Preferably, the alkene is propene, iso-propylene, 1-butene, iso-butylene or 1-pentene. Also of interest as substrates are alkenes and cycloalkenes which are synthetic intermediates along pathways to prepare compounds of interest. Cycloalkenes useful as substrates have a free allylic site, and include cyclopropene, cyclobutene, cyclopentene, cyclohexene, cycloheptene, and the like. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about $-20°$ C. to about $+20°$ C., or at elevated temperatures, for example, from about $+30°$ C. to about $+110°$ C., as well as at reduced or elevated pressures. The reaction may be carried out in a batch operation or continuously.

The present invention further provides a method of preparing a ketone from an alkene or cycloalkene wherein said alkene or cycloalkene is optionally mono-, di- or trisubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

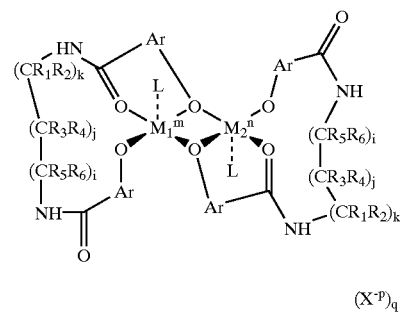

wherein $M_1$ and $M_2$ are independently selected from the group consisting of Fe, Co, Mn and Ru; wherein nm+n is 4 or 5; wherein p is 1 or 2, and q is 0, 1 or 2 such that $m+n-4=p \times q$; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (ill) $R_5$ and $R_6$ independently and optionally are linked covalently and together with the respective adjoining C atom comprise a spirocylic ring; wherein i, j and k are integers such that $2 \leq i+j+k \leq 4$ wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the ketone.

In a certain embodiment, the oxygen atom donor used in the method is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

In the practice of the invention, alkenes which are useful as substrates for the method of oxidation have an unsubstituted allylic site, and may be linear, branched or cyclic, and may be liquid or gaseous. Preferably, the alkene is propene, iso-propylene, 1-butene, iso-butylene or 1-pentene. Also of interest as substrates are alkenes and cycloalkenes which are synthetic intermediates along pathways to prepare compounds of interest. Cycloalkenes useful as substrates have a free allylic site, and include cyclopropene, cyclobutene, cyclopentene, cyclohexene, cycloheptene, and the like. Solvents which are suitable for conducting the oxidation reaction include any organic solvent in which the substrate is partially or fully soluble, and preferably include chlorinated solvents, such as dichloromethane, dichloroethane, trichloroethylene, tetrachloromethane, etc., either alone or in a mixed solvent system with an organic dipolar solvent, such as N,N-dimethylformamide or N,N-diethylformamide.

The amount of catalyst present in the reaction medium may suitably be in the range from about 0.001 to about 12% by weight, though typically from about 0.1 to about 5%, based on the weight of the reactants. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

The present invention also provides a method of preparing a binuclear metal complex having the structure:

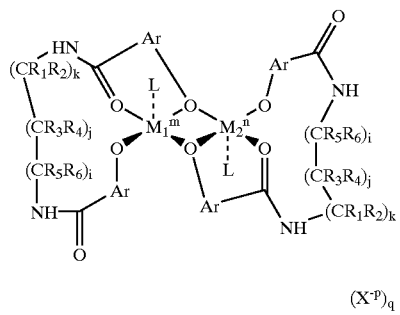

$$(X^{-p})_q$$

wherein $M_1$ and $M_2$ are independently selected from the group consisting of Fe, Co, Mn and Ru; wherein m and n are independently 2 or 3; wherein p is 1 or 2, and q is 0, 1 or 2 such that in m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, which comprises:

(A) preparing a dilithio, disodio or dipotassio salt of a ligand having the structure:

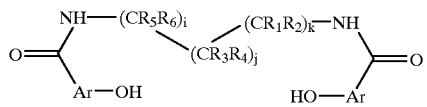

wherein $R_1$, $R_2$, $R_3$, $R_4$, $R_5$, $R_6$, i, j, k and Ar are defined as above; and (B) contacting the salt formed in step (A) with an approximately equal amount of $\{M_1^m/M_2^n\}(L)_2(X^{-p})_q(S)_2$ wherein $M_1$, $M_2$, L and X are defined as above; wherein m and n are each +2; and p×q=m or n; wherein S is a solvent selected from the group consisting of a linear or branched alkyl alcohol and water; under suitable conditions to form the binuclear metal complex.

In one embodiment, the method is useful to prepare a complex wherein wherein $M_1$ and $M_2$ are Fe; and wherein m and n are +2. In another embodiment, the method generates a complex wherein i and j are 1, and k is 0; and $R_1$, $R_2$, $R_3$, $R_4$, $R_5$ or $R_6$ are methyl. In a favored embodiment, the complex contains N-methylimidazole as the ligand L. The method described may advantageously be carried out wherein the ligand and the resulting binuclear complex are optically active.

Step (A) is carried out by methods known in the art, for example, as set forth in Anson et al., *J. Amer. Chem. Soc.*, 1984, 106, 4460. Step (B) is performed in dipolar organic solvents including any organic solvent in which the reagents are substantially or fully soluble, and preferably include acetonitrile, proprionitrile, butyronitrile, etc., either alone or more favorably in a mixed solvent system with an alcoholic co-solvent, such as methanol or ethanol, typically present to the extent of 1–5% by volume.

The reaction is preferably carried out under anaerobic conditions. The reaction is ordinarily and favorably performed at ambient temperatures and pressures, but may be performed at reduced temperatures, for example, from about −20° C. to about +20° C., or at elevated temperatures, for example, from about +30° C. to about +110° C., as well as at reduced or elevated pressures. The reaction may be carried out in a batch operation or continuously.

All patents, applications, articles, publications and test methods mentioned above are hereby incorporated by reference.

Many variations of the present invention will suggest themselves to those skilled in the art in light of the above detailed description. Such obvious variations are within the full intended scope of the appended claims. For example, the binuclear metal complex of the invention may comprise either five-coordinate or six-coordinate metal centers. When the metal centers are six-coordinate, the additional ligation site may be occupied by a solvent molecule, such as a water, methanol, ethanol, isopropanol, tetrahydrofuran, N,N-dimethyl formamide, or another solvent containing an unshared pair of electrons.

The present invention will be better understood from the Materials and Methods which follow. However, one skilled in the art will readily appreciate that the specific methods and results discussed are merely illustrative of the invention as described in the claims which follow thereafter.

Experimental Section

General Data. Analytical gas chromatography was performed on a Hewlett Packard 5890 Series II instrument equipped with a methyl silicon capillary column (50 m×0.25 mm i.d.) and a flame ionization detector. Peak areas were measured by electronic integration using a Hewlett-Packard 3396 Series II integrator. Mass spectra were taken on a Hewlett Packard 5890 Series II instrument interfaced to a Hewlett Packard 5971 A mass selective detector. Electronic absorption spectra were measured on a Perkin-Elmer Lambda 6 spectrometer in the 280–900 nm range, while infrared spectra were collected from KBr pellets on a Nicolet 5SX FT-IR spectrometer. $^1$H NMR spectra were recorded on a GE QE-Plus 300 MHz spectrometer. Chemical shift values are reported relative to the internal standard $Me_4Si$.

The substrates used in these studies (cyclohexene, cis-stilbene, trans-silbene, phenylmethyl sulfide, cyclohexane, cycloheptane, adamantine, methyl cyclohexane, 2,2,3,3, tetramethylbutane, norbornene, toluene and benzene) were purchased from Aldrich and purified by standard methods when necessary. [Perrin, 1988 #1508] Thianthrene 5-oxide was synthesized by literature procedures. [Ballistreri, 1991 #1569] All solvents were purified and dried prior to use by standard methods. [Perrin, 1988#1508] Dimethylformamide (Burdick & Jackson) was dried over activated 3 Å molecular sieves for 4 days and fractionally distilled under dynamic vacuum. Methanol (99%, Mallinckrodt) was dried over $Mg(OMe)_2$ and distilled immediately before use. Dichloromethane (Mallinckrodt) and acetonitrile (Baker) were dried by refluxing over $CaH_2$ under an inert ($N_2$) atmosphere and distilled immediately before use. Elemental analyses were done by Robertson Microlit Laboratories. All work was performed under anaerobic conditions using standard schlenk or inert atmosphere box techniques.

EXAMPLE 1

Iron Complexes. The non-heme iron complexes $[Fe^{2+}(H_2bamb)_2(N\text{-MeIm})_2]$, 1, $[Fe^2+Fe^3+(H_2bamb)_2(N\text{-MeIm})_2]I$, 2, and $[Fe_2^{3+}(H_2bamb)_2(N\text{-MeIm})_2]I_2$, 3 were prepared as previously reported. [Mukerjee, 1997 #$931]

Iodosylbenzene. Iodobenzene (Aldrich, 5.5 mL, 0.05 mol) was added to a solution of acetic anhydride (Aldrich, 61 mL, 0.65 mol) which had been stirred with 30% hydrogen peroxide (Aldrich, 14 mL) for 4 hours at 40° C. After reacting overnight at 40° C., the excess solvent was removed under reduced pressure. Upon cooling to 4° C., the resulting diacetate was obtained as a white solid which was then thoroughly dried under vacuum to yield 12.0 grams of $PhI(OAc)_2$ (75% yield). [Sharefkin, 1973 #1511] Hydrolysis of the diacetate with aqueous sodium hydroxide by literature methods allowed the isolation of OIPh. [Saltzman, 1973 #1512] Samples were stored at 4° C. and replaced every 2 months.

EXAMPLE 2

[$^{18}O$] Iodosylbenzene. $^{18}OIPh$ was synthesized by the method of Hill et al. [Schardt, 1983 #963] Yellow iodosylbenzene (0.5 g, 2.27 mmol) was stirred for 15 minutes with 15 mL of methanol. After the immediate formation of a milky white suspension, the compound dissolved over 3 hours to give a homogeneous solution. Molecular sieves (3 Å pore size, 1.5 g) were added and the mixture was stirred for an additional 2 hours. After filtration to remove the sieves, all solvent was removed and the resultant white solid was dried under vacuum for 10 h. The solid residue was dissolved in 25 mL hot hexane (freshly distilled from $P_2O_5$) and cooled to −70° C. in a 2-propanol/dry ice bath which lead to the isolation of white, crystalline iodobenzene dimethoxide (0.42 g, 68%).

$PhI(OMe)_2$ (0.2 g, 0.75 mmol) was suspended in 1.5 mL of ether and treated with 0.05 mL (2.6 mmol) of 70% $^{18}O$-labeled water (Cambridge Isotope Laboratory), resulting in the immediate formation of a yellow solid. The solution was stirred for 30 minutes, the solvent removed in vacuo and the solid dried overnight. The solid was then suspended in ether and collected by filtration. The resulting solid was washed with ether and then acetone before being dried under vacuum. The isolated yield was 0.15 g (93%). IR data show the expected peaks at 737, 686 and 460 $cm^{-1}$. The $^{18}O$ content was found to be 64±2% based on mass spectroscopy analysis of triphenylphosphine oxide synthesized by reacting the labeled iodosylbenzene with triphenylphosphine dissolved in dichloromethane.

EXAMPLE 3

Peracid Decomposition Reactions. Phenylperacetic acid (PPAA) was synthesized from phenylacetyl chloride and alkaline hydrogen peroxide by literature methods. [McDonald, 1970 #1513; White, 1980 #959] The peracid was standardized iodometrically by adding a known aliquot of peracid to a buffered 0.1 M sodium iodide solution in 95% ethanol followed by spectrophotometric determination of the concentration of triiodide ($\epsilon_M 358$ nm=$2.5\times10^4$) following the methods of Bruice et al. [Bruice, 1983 #953] Phenylperacetic acid activity was >85% in all cases; variations in peracid activity had no influence on the observed experimental results. 2,4,6-Tri-tert-butylphenol (TBPH) (Aldrich) was recrystallized several times from 95% ethanol until the solution in ethanol was colorless. Diazomethane was synthesized by the method of DeBoer et. al. [DeBoer, 1963 #952][WARNING: Although no accidents occurred in any attempts to make this compound, extreme precaution should be taken at all times.]

The reaction time course for PPAA decomposition was determined by monitoring the reaction of methanolic solutions of the iron complexes with PPAA in the presence of 2,4,6-tri-tert-butylphenol (TBPH), which forms the stable TBP. radical ($\epsilon_M 400$nm=1200). In a typical reaction performed under strict anaerobic conditions, 1 mL of a methanolic solution of PPAA (0.15M) and TBPH (2.5M) was placed in one compartment of a split UV/vis optical cell while the other compartment contained 1 mL of the appropriate iron complex (2 mM). After recording the baseline, the two solutions were mixed to afford a final ratio of 1:75:1250 of catalyst:PPAA:TBPH and the spectrum monitored at 630 nm for 3 hours. Parallel control reactions were also performed with the absence of iron catalyst. The difference between the catalyzed and uncatalyzed reactions allowed determination of the turnover number; turnover numbers were given by {TBP.} (cat)−TBP. (control)}/{2 [catalyst]}. Less than 10% of active PPAA remained at the end of the reactions.

Determination of the mode of cleavage of the percarboxylic acid peroxo bond was carried out as follows. Equal volumes of methanolic solutions of the iron complexes (0.8 mM) and PPAA (60 mM) were mixed (final catalyst: PPAA ratios of 1:75) in Wheaton glass serum bottles and sealed under an inert atmosphere. Upon completion of the reactions (10 h), all reaction solutions were treated with 1.5 mL of a freshly prepared solution of $CH_2N_2$ in ether and allowed to incubate for 1 hour. The products were analyzed by gas chromatography after venting the reaction mixtures inside an inert atmosphere box. Gradient temperature programs allowed baseline resolution of chlorobenzene (standard, 14.2 minutes), methyl phenylacetate (18.3 minutes), bibenzyl (20.7 minutes), benzyl alcohol (16.9 minutes), toluene (12.5 minutes), and benzaldehyde (16.0 minutes). Other potential benzyl radical based products (benzylphenyl acetate) as well as indirect oxidation products of benzyl alcohol and benzaldehyde (benzoic acid, methyl benzoate and phenyl methyl ether) were also examined. Identification of all products was made by comparison of retention times (catalytic reactions vs. Authentic standards) followed by co-injection of authentic standards with the reaction mixture. The expected reaction products were all shown to be stable to the gas chromatography conditions. Each sample was analyzed at least three times and each reported value is an average of a minimum of two experiments.

EXAMPLE 4

Catalytic Reactions. General Procedures. All reactions of iodosylbenzene with substrates catalyzed by the non-heme iron complexes were performed in Wheaton glass serum bottles (10 mL) equipped with a stirring bar and sealed with buyl rubber stoppers and aluminum caps. All reactions were performed under strict anaerobic conditions ($N_2$ atmosphere) in an inert atmospher box; all reagents and solutions were rigorously deoxygenated prior to use. Iodosylbenzene was added in one aliquot ot vials that contained the premeasured quantities of iron complex, substrate and solvent (10% DMF/dichloromethane). No attempts were made to optimize yield based on rate of OIPh addition. Upon the addition of OIPh, the vials were sealed and kept stirring in the inert atmosphere box for 8–10 hours.

Reaction mixtures were worked up by centrifuging the suspensions to remove unreacted iodosylbenzene and immediately freezing the homogeneous solutions in liquid $N_2$. Gas chromatographic analyses 9GC and GC-MS) were performed on aliquots withdrawn directly from the clarified reaction mixtures.

All starting substrates were checked by gas chromatography or NMR spectroscopy to ensure that no oxidation products were present before the reactions. Purification, when necessary, was performed by standard techniques and its effectiveness verified by spectroscopy. [Perrin, 1988 #1508] Yields were determined by gas chromatography using internal standard methods. Parallel control reactions, performed under identical reaction conditions for each substrate, in which the non-heme iron complexes were omitted showed little or not product formation. Final reported yields were corrected for any low level of non catalyzed product formation. Products were verified through the use of authentic samples and GC-MS analysis. Iodobenzene was recovered in quantitative yields for all reactions. All reactions were done at ambient temperature.

EXAMPLE 5

Reaction of Iodosylbenzene with Organic Substrates Catalyzed by $[Fe_2^{2+}(H_2bamb)_2(N\text{-}MeIm)_2]$, (1), $[Fe^2+Fe^{3+}(H_2bamb)_2(N\text{-}MeIm)_2]I$, (2), and $[Fe_2^{3+}(H2bamb)_2(N\text{-}MeIm)_2]I_2$, (3). All reactions were performed with [iron complex]: OIPh:substrate of 1:500:2500 with [iron complex]=1 nM unless otherwise stated. The anaerobic reactions were initiated by the addition of a single aliquot of iodosylbenzene (0.11 g, 0.5 mmol) to a 1 mL (10% DMF/dichloromethane) solution of the iron complex ($[Fe_2^{2+}(H_2bamb)_2(N\text{-}MeIm)_2]$, 1, 1 $\mu$mol, 0.98 mg; $[Fe^2+Fe^3+(H_2bamb)_2(N\text{-}MeIm)_2]I$, 2, 1 $\mu$mol, 1.11 mg; $[Fe_2^{3+}(H_2bamb)_2(N\text{-}MeIm)_2]I_2$, 3, 1 $\mu$mol, 1.24 mg) and the appropriate substrate (2.5 mmol). Immediately after working up the reaction, chlorobenzene was added as an internal standard and the mixtures were analyzed by gas chromatography (methyl silicone column, 40–240° C. at 12° C./min). Reported yields are corrected for any low level uncatalyzed reactions and are reported relative to iodosylbenzene usage as quantified by measurement of iodobenzene. All products were compared to authentic standards and analyzed by both gas chromatographic and mass spectral techniques.

Analogous methods were used for the oxidation of phenylmethyl sulfide except that the reaction was performed with [iron complex]: OIPh: substrate of 1:5000:25000 with [iron complex]=0.1 mM.

EXAMPLE 6 cis-Decalol and trans-Decalol. cis-Decalol and trans-decalol were synthesized by the oxidation of cis-decahydronapthalene (Aldrich) and trans-decahydronapthalene (Aldrich) by literature methods. [Wiberg, 1961 #965] The respective hydrocarbon (1 g, 52.7 mmol) was added to a solution of sodium dichromate (Aldrich, 10 g, 33.5 mmol) dissolved in 40 mL water and 25 g of 72% perchloric acid in enough acetic acid to make a total volume of 200 mL. The mixture was stirred at 8° C. for 1 h and then extracted with 3×50 mL portions of dichloromethane. The organic extracts were washed with a saturated sodium bicarbonate solution and then dried over potassium carbonate. Vacuum distillation gave a colorless liquid that was dissolved in aqueous ethanol and crystallized at $-20°$ C. $^1$H NMR spectra and mass spectral fragmentation patterns are as reported in the literature. [McClusky, 1977 #964]

Oxidation of cis-and trans-decahydronapthalene were performed as described above with [iron complex]: OIPh-:substrate of 1:500:2500 and [iron complex]=1 mM. Identification of cis-9-decalol, trans-9-decalol, 1-decalol and 2-decalol were made by gas chromatographic and mass spectral techniques using authentic samples (Aldrich) for comparison.

EXAMPLE 7

Deuterated Norbornanes. Norbornylene (Aldrich, 1 g, 10.6 mmol) was hydrogenated in 5 mL of diethyl ether with deuterium (40 psi) over 5% Pd/carbon. After removal of the catalyst by filtration, the solvent was removed and the residue sublimed, affording pure norbornane-exo, exo-2,3-$d_2$. Similarily, norbornane-exo, exo, exo, exo-2,3,5,6-$d_4$ was synthesized by the catalytic hydrogenation of freshly distilled norbornadiene (Aldrich, 1 g, 10.8 mmol) in 5 mL of diethyl ether with deuterium (40 psi) over 5% Pd/carbon.Mass spectra revealed that norbornane-exo,exo-2,3-$d_2$ contained 95% $d_2$. content and 5% $d_1$ while norbornane-exo, exo, exo, exo-2,3,5,6-$d_4$ contained 90% $d_4$ and 10% $d_3$. Integration of the $^1$H NMR spectra of norbornene, norbornane-exo,exo-2,3-$d_2$, and norbornane-exo,exo,exo,exo-2,3,5,6-$d_4$ indicated that $\geq$98% of the deuterium was in the exo positions. [McClusky, 1977 #964; Groves, 1978 #718]

EXAMPLE 8

Inter- and Intra-Molecular Kinetic Isotope Effect Measurements. Intermolecular kinetic isotope effect measurements were performed in two separate reactions with cyclohexane and cycloheane-$d_{12}$ (Aldrich), iodosylbenzene and $[Fe_2^{2+}(H_2bamb)_2(N\text{-}MeIm)_2]$, 1, in 10% DMF/dichloromethane using cyclooctane as an internal standard ([1]:[OIPh]:substrate=1:500:2500, with [1]=1 mM). The ratio of the product distribution of cyclohexanol:cyclooctanol and cyclohexano)-$d_{12}$:cyclooctanol yielded the desired $k_H/k_D$ for benzene and benzene-$d_6$ (Aldrich).

The intramolecuar $k_H/k_D$ was determined for the reactions of iodosylbenzene with norbornane (Aldrich), norbornane-exo,exo-2,3-$d_2$, and norbornane-exo,exo,exo,exo-2,3,5,6$d_4$ ([1]:OIPh:substrate=1:500:2500, [1]=1 mM) in 0.2 mL 10% DNF/dichloromethane. [Groves, 1978 #718; McClusky, 1977 #1964 The trimethylsilyl ether derivatives of the norborneos were prepared by the addition of O,N,-bis-trimethylsilylacetamide (Aldrich) to the reaction vials with a gas tight syringe to allow analysis of the reaction products by gas chromatographic-mass spectral techniques. O,N,-bis-trimethylsilylacetamide is extremely hygrosocpic and proper precautions should be taken not to expose the solution to air. The silyl ether products exhibited base peaks correspond tin to $M^+$—$CH_3$ which could be analyzed for deuterium content with confidence.

Discussion

The reaction of equimolar quantities of trans-$Fe^{2+}$(N-MeIm)$_2$(Cl)$_2$(MeOH)$_2$[18,19] and the dilithium salt of 2,3-bis(2-hydroxybenzamido)2,3-dimethylbutane, H$_4$bamb (FIG. 1),[24] in anhydrous 1% methanol-actonitrile under anaerobic conditions afforded [Fe$_2$$^{2+}$(H$_2$bamb)$_2$(N-MeIm)$_2$], 1,[25a] (60% yield) as a pale yellow microcrystalline product. Isothermal distillation techniques[26,27] indicate that 1 has a molecular weight of ≈1100, consistent with its dimeric formulation. EPR spectra of 1 show a $g_{eff}$≈16 signal, suggesting a ferromagnetically coupled S=4 core as previously reported for an analogous binuclear system.[19] Cyclic voltammetry experiments performed in DMF show two coupled 1e-oxidation/reduction processes; a scan-rate dependent quasi-reversible process at −310 mV (NHE) and an electrochemically reversible couple at −690 mV (NHE), giving $K_{com}$=2.7×10$^6$. Repetitive scans showed no significant decrease in either cathodic or anodic current; ligand centered redox behavior was observed outside this region of interest and did not interfere with the metal-based processes. The scan rate dependence of $\Delta E_p$, attributed to kinetic effects, allowed the measurement of an intrinsic rate constant, k=2×10$^5$, assuming pseudo-first-order kinetics. This rate constant, thought to reflect a structural change, is independent in [1] over a 3-fold range. A similar process was demonstrated in the redox transformation (−10 and −260 mV) of [Fe$_2$$^{2+}$(H$_2$Hbab)$_2$(N-MeIm)$_2$], which differs from 1 in that the binucleating ligand contains an o-phenylenediamine moiety in place of the 2,3-diamino-2,3-dimethylbutane group.[19] The stoichiometric I$_2$ titration of 1, as monitored by UV/vis spectroscopy, shows the clean formation of [Fe$^{2+}$, Fe$^{3+}$], 2, with an isosbestic point at 325 nm; the titration of one additional oxidizing equivalent readily converts 2 to [Fe$^{3+}$, Fe$^{3+}$], 3, with isosbestic points at 457 nm and 335 nm. Solution molecular weight characterizations of 2 and 3 are consistent with their binuclear formulations.[25] Both 2 and 3 give rise to broadened g=4.3 signals in their EPR spectra.

Catalytic atom transfer reactions (Table 1) were investigated under strict anaerobic conditions using OIPh as oxygen atom donor molecule and cyclohexane, cyclohexene, methyl phenyl sulfide and toluene as substrates in 10% DMF/CH$_2$Cl$_2$.[28] All complexes were stable in the absence of iodosylbenzene for over 12 hours. Parallel control reactions (absence of catalyst) were used to correct for non-metal mediated products. Iodobenzene was recovered in quantitative yields in all reactions. The products obtained from the oxidation of cyclohexane with 1 and OIPh (cyclohexanol (57), cyclohexanone (1), and chlorocyclohexane (57)) clearly indicate the ability of 1 to catalyze the oxidation of alkanes by oxygen atom donor molecules. The effect of core oxidation states is evident from the reaction of 2, which produces chlorocyclohexane (38) as the dominant product and only trace amounts of cyclohexanol (1). The fully oxidized complex, 3, produces only low levels of chlorocyclohexane (13). The requirement for at least one ferrous center is more evident in the catalytic oxidations of olefins such as cyclohexene. Both 1 and 2 yield primarily allylic oxidation products (cyclohexenol and cyclohexenone), although cyclohexene oxide represents a significant product (30% and 22%, respectively). Interestingly, reactions catalyzed by 3 produce only low levels of cyclohexenol, suggesting that the [Fe$^{3+}$, Fe$^{3+}$] core is not an effective oxygen transfer catalyst under these conditions. This conclusion is supported by results from the catalytic oxidation of PhSMe, where both 1 and 2 exhibit excellent catalytic ability. The two electron oxidation of sulfide is readily performed in the presence of a ferrous center while the ferric complex, 3, is inert as a sulfide oxidation catalyst. The binuclear compound 1 oxidizes toluene to primarily produce benzylic oxidation products with only minor levels of product resulting from attack of the aromatic ring, while 2, very interestingly, gives rise to predominantly aromatic ring oxidation products. Under identical conditions, simple $Fe^{2+}$ and $Fe^{3+}$ salts in the presence of OIPh were unable to catalyze any of these reactions.[29] The intermolecular kinetic isotope effect for alkane C—H oxidation was determined by the competitive oxidation of cyclohexane and cyclohexane-d$_{12}$ ($k_H/k_D$=2.2).[30] This small intermolecular KIE is consistent with some,[31-33] but not all,[34] studies for the oxidation of alkanes by MMO and is indicative of only a minor contribution from C—H bond breaking in the rate determining step of substrate oxidation.

A comparison with the product distributions obtained from OIPh oxidation reactions catalyzed by iron porphyrins, whose mechanisms invoke a reactive high valent [Fe$^{4+}$=O] species,[21-23] is presented in Table 1. While Fe(TPP)Cl catalyzed oxidations of cyclohexane do not form any chlorinated product in the presence of CH$_2$Cl$_2$, brominated products are reported in the reaction of cycloheptane in CH$_2$Br$_2$.[35] Furthermore, the ability of 1 and 2 to catalyze the oxidations of alkanes is substantially quenched when polar solvents such as CH$_3$CN are used instead of hydrophobic solvents such as CH$_2$Cl$_2$. An analogous phenomenon, ascribed to competition between solvent and the oxygen atom donor molecules for the labile site on the iron center, is also known for the porphyrin systems.[36] In the absence of substrate, 1 reacts with OIPh to yield a $\mu$-oxo Fe$^{3+}$ dimer, which is inert as an oxygen-atom transfer catalyst. Differences in the catalytic chemistry observed for 1 and 2 and that previously reported for [Fe$_2$$^{2+}$(H$_2$Hbab)$_2$(N-MeIm)$_2$] are thought to reflect the greater ease by which the core redox properties induced by the H$_2$bamb$^{2-}$ ligand support formation of the reactive intermediate.[18,19]

These data demonstrate for the first time the ability of simple binuclear non-heme iron complexes containing at least one ferrous center to act as efficient oxygen-atom transfer catalysts using OIPh as the donor molecule. The chemistry exhibited by 1 and 2 clearly mimics many of the reactions heretofore seen only for heme systems, indicating that simple N/O ligand environments are adequate to support oxidative chemistry by oxygen atom donor molecules. Although the reactive intermediate(s) responsible for the observed alkane, arene, alkene and sulfide oxidation chemistry exhibited by 1 and 2 is not as yet unambiguously defined, its reactivity pattern is analogous to that observed in CytP-450 enzyme chemistry, synthetic high-valent iron-oxo radical cation porphyrin model species,[22,23] and the putative binuclear high-valent iron species observed in the catalytic cycle of MMO.[4,5] Current efforts are designed to examine the effect of alternative oxygen-atom donors and metal based redox potential on catalysis, elucidate the intimate mechanism of oxygen-atom transfer via isotopic labeling studies, and identify and spectroscopically characterize the reactive intermediate(s) responsible for this chemistry.

REFERENCES (1) Caradonna, J. P.; Stassinopoulos, A. *Adv Inorg Biochem* 1994, 9, 245–315.
(2) Stassinopoulos, A.; Mukerjee, S.; Caradonna, J. P. *Reactivity Models for Dinuclear Iron Metalloenzymes: Oxygen Atom Transfer Catalysis and Dioxygen Activation*; Stassinopoulos, A.; Mukerjee, S.; Caradonna, J. P., Ed.; American Chemical Society; Washington D.C., 1994; Vol. 246, pp. 83–120.

(3) Rosenzweig, A. C.; Frederick, C. A.; Lippard, S. J.; Nordlund, P. *Nature* 1993, 366, 537–43.
(4) Feig, A. L.; Lippard, S. J. *Chem. Rev.* 1994, 94, 759–805.
(5) Waller, B. J.; Lipscomb, J. D. *Chem. Rev.* 1996, 96, 2625–2658.
(6) Rosenzweig, A. C.,; Feng, X.; Lippard, S. J. *Applications of Enzyme Biotechnology;* Kelly, J. W., Baldwin, T. O. Ed.; Plenum Press: New York, 1991, pp. 69–85.
(7) Barton, D. H .R.; Beck, A. H.; Taylor, D. K. *Tetrahedron* 1995, 51, 5245–5254.
(8) Vincent, J. M.; Menage, S.; Lambeaux, C.; Fontecave, M. *Tetrahedron Lett.* 1994, 35, 6287–6290.
(9) Barton, D. H. R.; Doller, D. *Acc. Chem. Res.* 1992, 25, 504.
(10) Buchanan, R. M.; Chen, S.; Richardson, J. F.; Bressan, M.; Forti, L.; Morvillo, A.; Fish, R. H. *Inorg. Chem.* 1994, 33, 3208–3209.
(11) Leising, R. A.; Kim, J. H.; Perez, M. A.; Que, L. *J. Am. Chem. Soc.* 1993, 115, 9524–9530.
(12) Fish, R. H.; Oberhausen, K. J.; Chen, S.; Richardson, J. F.; Pierce, W.; Buchanon, R. M. *Catalysis Letters* 1993, 18, 357–365.
(13) Kim, J.; Harrison, R. G.; Kim, C.; Que, L. J. *J. Am. Chem. Soc.* 1996, 118, 4373–4379,
(14) Perkins, M. J. *Chem. Soc. Rev.* 1996, 25, 229–236.
(15) Minisci, F.; Fontana, F.; Araneo, S.; Recupero, F.; Zhao, L., *SynLett* 1996, 119–125.
(16) Newcomb, M.; Simakov, P. A.; Park, S.-U. *Tetrahedron Letters* 1996, 37, 819–822.
(17) (a) Arends, I. W. C. E.; Ingold, K. U.; Wayner, D. D. M. *J. Am. Chem. Soc.* 1995, 117, 4710–4711. (b) MacFaul, P. A.; Arends, I. W. C. E.; Ingold, K. U.; Wayner, D. D. M. *J. Am. Chem. Soc.* 1995, 117, 4710–4711. (b) MacFaul, P. A.; Arends, I. W. C. E.; Ingold, K. U.; Wayner, D. D. M. *J Chem. soc. Perkin Trans.* 2, 1997, 135–145.
(18) Stassinopoulos, A.; Caradonna, J. P. *J. Am. Chem. Soc.* 1990, 112, 7071–7073.
(19) Stassinopoulos, A.; Schulte, G.; Papaefthymiou, G. C.; Caradonna, J. P. *J. Am. Chem. Soc.* 1991, 113, 8686–8697.
(20) Abbreviations: $H_4Hbamb$, 2,3-bis(2-hydroxybenzamido)2,3-dimetbylbutane; N-MeIm, N-methyl imidazole; PPAA, phenylperacetic acid; TPP, tetraphenylporphyrin; $H_4Hbab$, 1,2-bis(2-hydroxybenzamido)benzene.
(21) McMurry, T. J.; Groves, J. T. *Cyt P450 model systems;* McMurry, T. J., Groves, J. T., Ed.; Plenum Press: New York, 1986, pp. 1–28.
(22) Meunier, B. *Chem. Rev.* 1992, 92, 1411–1456.
(23) Sono, M.; Poach, M. P.; Coulter, E. D.; Dawson, J. H. *Heme-Containing Oxidases;* Sono, M.; Poach, M. P. Coulter, E. D.; Dawson, J. H., Ed.; Am. Chem. Soc. Press: Washington, D.C.,; 1996, Vol. 96, pp. 2841–2888.
(24) Anson, F. C.; Christie, J. A.; Collins, T. J.; Coots, R. J.; Furutani, T. T.; Gipson, S. L.; Keech, J. T.; Kraft, T. E.; Santasiero, B. D.; Spies, G. H. *J. Am. Chem. Soc.* 1 984, 106, 4460–4472.
(25) (a) $[Fe_2^{2+}(H_2Hbamb)_2(N-MeIm)_2]$ solvated, 1: Anal. Calcd for $C_{55}H_{72}N_9O_{13}Fe_2$: C, 55.90; H, 6.10; N, 10.68; Fe, 9.49. Found: C, 55.69; H, 5.70; N, 10.86; Fe, 9.43; UV/vis (DMF): $\lambda_{max}$ ($\epsilon_M$) 314 nm (20,000); IR: $v_{amide}NH=3430$ $cm^{-1}$, $v_{amide}CO=1611$ $cm^{-1}$; Electrochemistry (NHE); quasi reversible redox process; −690 mV, $\Delta E=220$–470 mV with scan rate 25–125 $mVs^{-i}$, reversible process: −310 mV, $\Delta E=70$ mV. (b) $[Fe_2^{2+}FE^{3+}(H_2Hbamb)_2(N-MeIm)_2](I^-)$ solvated, 2: Anal. Calcd. for $C_{55}H_{72}N_{10}O_{15}ICl_2FE_2$; C, 49.18; H, 5.36; N, 10.43; Fe, 8.31. Found: C, 48.67, H, 5.27: N, 10.37; Fe, 8.10: UV/vis (DMF); $\lambda_{max}$ ($\epsilon_M$)301 nm (25,000), 436 nm (7,000); IR: $v_{amide}NH=3430$ $cm^{-1}$; $V_{amide}CO=1654$ $cm^{-1}$; EPR: gelf= 4.3; (c) $[Fe_2^{3+}(H_2Hbamb)_2(N-MeIm)_2](I^-)_2$ solvated, 3: Anal. Calcd. for $C_{55}H_{72}N_{10}O_{15}I_2Cl_2Fe_2$; C, 49.18; H, 5.36; N, 10.43; Fe, 8.31 Found: C, 48.67, H 5.27; N, 10.37; Fe, 8.10; UV/vis (DMF): (DMF) $\lambda_{max}$ ($\lambda_M$)=301 nm (25,000), 436 nm (7,000); IR: $v_{amide}NH=3430$ $cm_{-1}$, $v_{amide}CO=1654$ $cm_{-1}$; EPR; gelf=4.3; (c) $Fe_2^{3+}(H_2bamb)_2(N-MeIm)_2$ solvated, 3: Anal. Calcd. for $C_{55}H_{72}N_{10}O_{15}I_2CL_2Fe_2$: C, 44.90, H, 4.90, N, 9.53, Fe, 7.60. Found: C, 44.22, H, 5.20, N. 9.71; Fe, 7.46; UV/vis (DMF): $\lambda_{max}$ ($\epsilon_M$)=301 nm (25,000), 470 nm (7,000; IR: $v_{amide}NH=3430$ $cm^{-1}$, $v_{amide}CO=1654$ $cm^{-1}$. Forms adduct with catechol DMF λ.max=560 nm).
(26) Signer, R. *Ann. Chem.* 1930, 478, 246.
(27) Clark, E. P. *J. Chem. Educ.* 1941, 820–821.
(28) All gas chromatographic analysis were performed on a Hewlett Packard Series 2 GC equipped with a methyl silicon capillary column and interfaced to a HP3396 series II integrator. Mass spectral analyses were performed on a HP 5971 Mass selective detector attached to a HP5890 Series 2 GC. Gradient temperature programs were used for baseline resolution of all products. Authentic samples were used to verify all retention times. Expected reaction products were stable to GC conditions.
(29) Studies using $FeCl_2$ and $FeCl_3$ were performed and analyzed by GC and GC/MS techniques using reaction conditions identical to those reported for 1–3 (Table 1) with catalyst: OIPh:substrate=1:500:2500 ([Catalyst]=1 mM; substrates=cyclohexane, cyclohexene, phenylmethyl sulfide, toluene). All reactions were performed in 10% $DMF/CH_2Cl_2$ under an inert $N_2$) atmosphere and followed for 12 hours.
(30) Cyclohexane and cyclohexane-$d_{12}$ studies were performed in two separate reactions with OIPh and 1; cyclooctane was used as an internal standard (1: OIPh:substrate=1:500:2500,[1]=1 mm). The ratio of the product distribution of cyclohexanol: cyclooctanol and deuterated cyclohexanol: cyclooctanol yields the desired $k_H/k_D$.
(31) Liu, K.; Johnson, C. C.; Newcomb, M.; Lippard, S. J. *J. Am. Chem. Soc.* 1993, 115, 939–947.
(32) Rataj, M. J.; Kauth, J. E.; Donnelly, M. I. *J. Biol. Chem.* 1991, 266, 18684–18690.
(33) Shimoda, M.; Okura, I. *J. Mol. Catal.* 1992, 72, 263–267.
(34) Green, J.; Dalton, H. *Biochem. J.* 1989, 259, 167–172.
(35) Groves J. T.; Nemo, T. E., *J. Am. Chem. Soc.* 1983, 105, 6243–6248.
(36) Linsey Smith, J. R.; Mortimer, D. N. *J. Chem. Soc. Chem. Commun.* 1985, 410–411.

What is claimed is:

1. A binuclear metal complex having the structure:

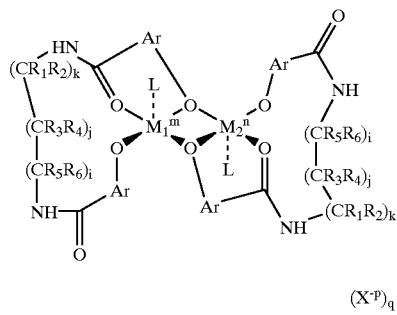

wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, hydrogen phosphate, dihydrogen phosphate, perchlorate, nitrate, triflate, p-tosylate, mesylate, formate, acetate, tartrate or citrate.

2. The binuclear complex of claim 1 wherein the complex is optically active.

3. The binuclear complex of claim 1 wherein $M_1$ and $M_2$ are Fe; wherein m and n are +2; wherein i and j are 1, and k is 0; and $R_1$, $R_2$, $R_3$, $R_4$, $R_5$ or $R_6$ are methyl.

4. The binuclear complex of claim 1 wherein L is N-methylimidazole.

5. A ligand having the structure:

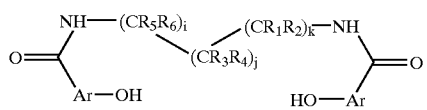

wherein $R_1$, $R_2$, $R_3$, $R_4$, $R_5$ and $R_6$ are independently and optionally substituted linear $C_1$–$C_6$ alkyl, $C_5$–$C_6$ cycloalkyl or phenyl; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, form ate, acetate, tartrate or citrate.

6. The ligand of claim 5 wherein i and j are 1, and k is 0; and $R_1$, $R_2$, $R_3$, $R_4$, $R_5$ or $R_6$ are methyl.

7. A method of preparing an alcohol from an alkane or cycloalkane wherein said alkane or cycloalkane is optionally substituted by an aryl, which comprises:

(A) dissolving the alkane or cycloalkane in a suitable solvent to form a solution; and (B) treating the solution with an oxygen atom donor in the presence of a binuclear metal complex having the structure:

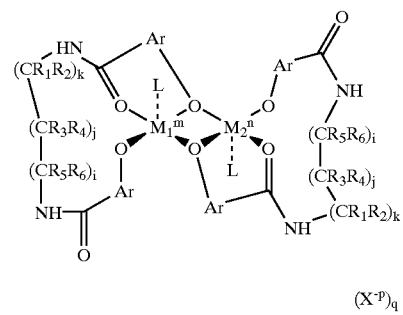

wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the alcohol.

8. The method of claim 7 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

9. A method of preparing an epoxide from an alkene or cycloalkene, wherein the alkene or cycloalkane is optionally mono-, di-, tri- or tetrasubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

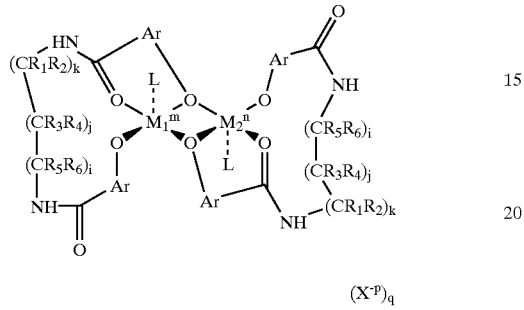

wherein $M_1$ and $M_2$ are independently selected from the group consisting of Fe, Co, Mn and Ru; wherein m+n is +4 or +5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i,j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the epoxide.

10. The method of claim 9 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

11. The method of claim 9 wherein the complex is optically active and the epoxide is a single enantiomer.

12. A method of preparing a sulfoxide from a dialkyl sulfide, alkyl aryl sulfide or diaryl sulfide wherein each alkyl is independently an optionally substituted $C_1$–$C_6$ alkyl, $C_3$–$C_9$ alkylalkenyl, or $C_5$–$C_6$ cycloalkyl, or the sulfide S atom interrupts an optionally substituted $C_5$–$C_{10}$ alkane ring, which comprises:

(A) dissolving the sulfide in a suitable solvent to form a solution; and (B) treating the solution with an oxygen atom donor in the presence of a binuclear metal complex having the structure:

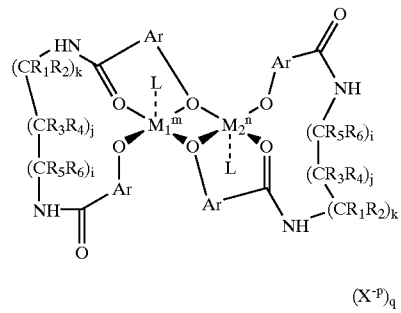

wherein $M_1$ and $M_2$ are independently selected from the group consisting of Fe, Co, Mn and Ru; wherein m+n is +4 or +5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that mn +n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the sulfoxide.

13. The method of claim 12 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

14. A method of preparing an arene alcohol from an arene wherein said arene is optionally substituted by an aryl, which comprises:

(A) dissolving the arene in a suitable solvent to form a solution; and (B) treating the solution with an oxygen atom donor in the presence of a binuclear metal complex having the structure:

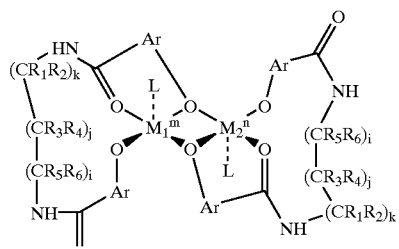

$(X^{-p})_q$

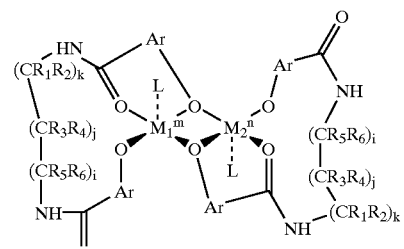

$(X^{-p})_q$ wherein $M_1$ and $M_2$ are independently selected from the group consisting of Fe, Co, Mn and Ru; wherein m and n are independently +2 or +3; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the arene alcohol.

15. The method of claim 14 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

16. The method of claim 14 wherein the arene is benzene, napthalene, anthracene or indene.

17. A method of preparing a sulfone from a dialkyl sulfide, alkyl aryl sulfide or diaryl sulfide wherein each alkyl is independently an optionally substituted $C_1$–$C_6$ alkyl, $C_3$–$C_9$ alkylalkenyl, or $C_5$–$C_6$ cycloalkyl, or the sulfide S atom interrupts an optionally substituted $C_5$–$C_{10}$ alkane ring, which comprises:

(A) dissolving the sulfide in a suitable solvent to form a solution; and (B) treating the solution with an oxygen atom donor in the presence of a binuclear metal complex having the structure:

wherein $M_1$ and $M_2$ are independently selected from the group consisting of Fe, Co, Mn and Ru; wherein m+n is +4; wherein p is 1 or 2, and q is 0, 1 or 2 such that m+n−4=p×q; wherein $R_1$, $R_2$, $R_3$, $R_4$, $R_5$ and $R_6$ are independently an optionally substituted linear $C_1$–$C_6$ alkyl, $C_5$–$C_6$ cycloalkyl or phenyl; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the sulfone.

18. The method of claim 17 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

19. A method of preparing a alcohol from an alkene or cycloalkene wherein said alkene or cycloalkene is optionally mono-, di- or trisubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

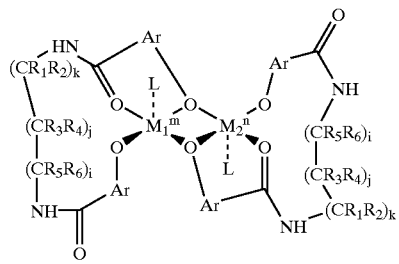

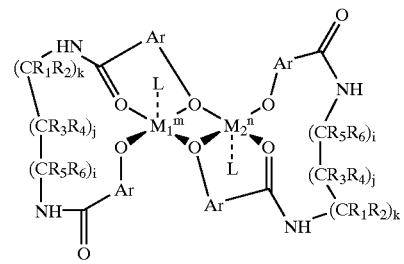

wherein $M_1$ and $M_2$ are independently selected from the group consisting of Fe, Co, Mn and Ru; wherein m+n is 4 or 5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the alcohol.

20. The method of claim 19 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

21. The method of claim 20 wherein the complex is optically active and the alcohol is a single enantiomer.

22. A method of preparing a ketone from an alkene or cycloalkene wherein said alkene or cycloalkene is optionally mono-, di- or trisubstituted independently with an optionally substituted linear $C_1$–$C_6$ alkyl, $C_5$–$C_6$ cycloalkyl or phenyl, which comprises:

(A) dissolving the alkene or cycloalkene in a suitable solvent to form a solution; and (B) treating the solution with an oxygen atom donor in the presence of a binuclear metal complex having the structure:

wherein $M_1$ and $M_2$ are independently selected from the group consisting of Fe, Co, Mn and Ru; wherein m+n is 4 or 5; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i, j and k are integers such that $2 \leq i+j+k \leq 4$; wherein p is 1 or 2, and q is 0, 1 or 2 such that m+n−4=p×q; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, under suitable conditions to form the ketone.

23. The method of claim 22 wherein the oxygen atom donor is iodosyl benzene, a peracid, N,N-dimethylaniline N-oxide, N,N-dimethyl-p-cyanoaniline N-oxide, periodate, t-butyl hydroperoxide, a peroxide or hypochlorite ion.

24. A method of preparing a binuclear metal complex having the structure:

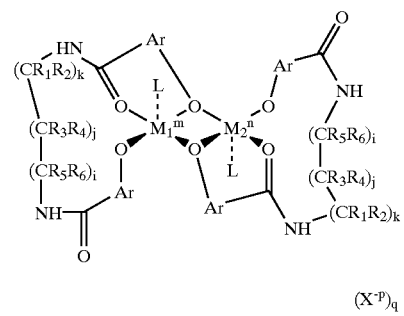

wherein $M_1$ and $M_2$ are independently selected from the group consisting of Fe, Co, Mn and Ru; wherein m and n are independently 2 or 3; wherein p is 1 or 2, and q is 0, 1 or 2 such that m+n−4=p×q; wherein $R_1$, $R_2$, $R_3$, $R_4$, $R_5$ and $R_6$ are independently a linear $C_1$–$C_6$ alkyl, $C_5$–$C_6$ cycloalkyl or phenyl optionally substituted by a linear or branched chain alkyl, alkoxy, alkoxycarbonyl, carboxamido, or halogen; wherein (i) $R_1$ and $R_2$, (ii) $R_3$ and $R_4$, or (iii) $R_5$ and $R_6$ independently and optionally are linked covalently and together with the respective adjoining C atom comprise a spirocylic ring; wherein i,j and k are integers such that $2 \leq i+j+k \leq 4$; wherein p is 1 or 2, and q is 0, 1 or 2 such that $m+n-4=p \times q$; wherein (i) $R_1$ or $R_2$ and $R_3$ or $R_4$, (ii) $R_3$ or $R_4$ and $R_4$ or $R_5$, or (iii) $R_1$ or $R_2$ and $R_5$ or $R_6$ independently and optionally are linked covalently and together with the respective adjoining C atoms comprise a fused ring; wherein Ar is 1,2-phenylene, 1,2- or 2,3-naphthylene or 1,2- or 2,3-anthracenylene, wherein said Ar is optionally substituted by $C_1$–$C_6$ alkyl or alkoxy; wherein L is N-methylimidazole, N-ethylimidazole, N-1-propylimidazole or N-phenylimidazole; and wherein X is fluorine, chlorine, bromine, iodine, borate, tetrafluoroborate, sulfate, hydrogen sulfate, carbonate, hydrogen carbonate, phosphate, hydrogen phosphate, dihydrogen phosphate, perchlorate, nitrate, triflate, p-tosylate, mesylate, formate, acetate, tartrate or citrate, which comprises:

(A) preparing a dilithio, disodio or dipotassio salt of a ligand having the structure:

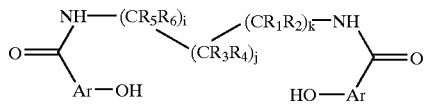

wherein $R_1$, $R_2$, $R_3$, $R_4$, $R_5$, $R_6$, i, j, k and Ar are defined as above; and (B) contacting the salt formed in step (A) with an approximately equal amount of $\{M_1^m/M_2^n\}(L)_2(X^{-p})_q(S)_2$ wherein $M_1$, $M_2$, L and X are defined as above; wherein m and n are each +2; and $p \times q = m$ or n; wherein S is a solvent selected from the group consisting of a linear or branched alkyl alcohol and water; under suitable conditions to form the binuclear metal complex.

25. The method of claim 24 wherein $M_1$ and $M_2$ are Fe; and wherein m and n are +2.

26. The method of claim 24 wherein i and j are 1, and k is 0; and $R_1$, $R_2$, $R_3$, $R_4$, $R_5$ or $R_6$ are methyl.

27. The method of claim 24 wherein L is N-methylimidazole.

28. The method of claim 24 wherein the ligand and the resulting binuclear complex are optically active.

* * * * *

UNITED STATES PATENT AND TRADEMARK OFFICE
CERTIFICATE OF CORRECTION

PATENT NO. : 6,395,904 B1
DATED : May 28, 2002
INVENTOR(S) : John P. Caradonna et al.

It is certified that error appears in the above-identified patent and that said Letters Patent is hereby corrected as shown below:

Column 1,
Please amend the second paragraph as follows:

-- This invention was made with government support under grant no. SGER CHE-949178 from the National Science Foundation, grant no. R29GM49871 from the National Institutes of Health, and grant no. DE-FG02-92ER14279 from the Department of Energy. Accordingly, the U.S. Government has certain rights in the invention. --

Signed and Sealed this

Fifth Day of October, 2004

JON W. DUDAS
*Director of the United States Patent and Trademark Office*